(12) United States Patent
Mabotuwana et al.

(10) Patent No.: US 11,289,188 B2
(45) Date of Patent: Mar. 29, 2022

(54) CONTEXT DRIVEN SUMMARY VIEW OF RADIOLOGY FINDINGS

(71) Applicant: KONINKLIJKE PHILIPS N.V., Eindhoven (NL)

(72) Inventors: Thusitha Dananjaya De Silva Mabotuwana, Yonkers, NY (US); Ye Xu, Milford, CT (US); Yuechen Qian, Briarcliff Manor, NY (US); Gabriel Ryan Mankovich, Yorktown Heights, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 229 days.

(21) Appl. No.: 14/769,480

(22) PCT Filed: Mar. 24, 2014

(86) PCT No.: PCT/IB2014/060096
§ 371 (c)(1),
(2) Date: Aug. 21, 2015

(87) PCT Pub. No.: WO2014/155273
PCT Pub. Date: Oct. 2, 2014

(65) Prior Publication Data
US 2016/0012319 A1    Jan. 14, 2016

Related U.S. Application Data

(60) Provisional application No. 61/806,550, filed on Mar. 29, 2013.

(51) Int. Cl.
*G06K 9/00* (2006.01)
*G16H 30/20* (2018.01)
(Continued)

(52) U.S. Cl.
CPC ............... *G16H 30/20* (2018.01); *G06K 9/72* (2013.01); *G06T 7/0014* (2013.01); *G16H 15/00* (2018.01);
(Continued)

(58) Field of Classification Search
CPC ..... G06K 9/72; G06F 19/321; G06F 19/3443; G06F 19/3487; G06T 7/0014; G06T 2207/30004
See application file for complete search history.

(56) References Cited

U.S. PATENT DOCUMENTS 8,023,704 B2    9/2011  Okira
8,521,561 B2    8/2013  Sasai et al.
(Continued)

FOREIGN PATENT DOCUMENTS

CN    102844761 A    12/2012
JP    2003108664 A    4/2003
(Continued)

*Primary Examiner* — Shefali D Goradia (57) ABSTRACT

A system, method and computer readable storage medium for generating a context driven summary view of medical findings by retrieving a current study including at least one image to be analyzed, extracting current context information from the current study and storing the current context information in a database and matching the current context information with prior context information from prior studies to return a set of relevant prior studies.

17 Claims, 11 Drawing Sheets

(51) Int. Cl.
  *G16H 15/00*  (2018.01)
  *G16H 50/70*  (2018.01)
  *G16H 30/40*  (2018.01)
  *G06K 9/72*  (2006.01)
  *G06T 7/00*  (2017.01)
(52) U.S. Cl.
  CPC ............. *G16H 30/40* (2018.01); *G16H 50/70* (2018.01); *G06T 2207/30004* (2013.01)

(56) References Cited

U.S. PATENT DOCUMENTS

| | | | |
|---|---|---|---|
| 8,934,695 B2 | 1/2015 | Sato et al. | |
| 9,008,390 B2 | 4/2015 | Takata et al. | |
| 2007/0133736 A1* | 6/2007 | Chen | A61B 6/00 378/5 |
| 2008/0016065 A1* | 1/2008 | Takaai | G06F 17/30011 |
| 2008/0104116 A1* | 5/2008 | Van Hoe | G06K 9/6267 |
| 2009/0187407 A1* | 7/2009 | Soble | G06F 19/3487 704/260 |
| 2010/0274776 A1 | 10/2010 | Iizuka | |
| 2013/0259350 A1 | 10/2013 | Sato et al. | |
| 2014/0089000 A1 | 3/2014 | Takata et al. | |
| 2014/0149407 A1 | 5/2014 | Qian | |

FOREIGN PATENT DOCUMENTS

| | | |
|---|---|---|
| JP | 2004305551 A | 11/2004 |
| JP | 2005027978 A | 2/2005 |
| JP | 2005160502 A | 6/2005 |
| JP | 2007072649 A | 3/2007 |
| JP | 2009080731 A | 4/2009 |
| JP | 2011018111 A | 1/2011 |
| JP | 2012053632 A | 3/2012 |
| JP | 2013211009 A | 10/2013 |
| JP | 2013214298 A | 10/2013 |
| WO | WO2011/132097 * | 10/2011 |
| WO | 2013001678 A1 | 1/2013 |
| WO | 2013018363 A1 | 2/2013 |
| WO | 2013018363 A1 | 3/2015 |

* cited by examiner

| Current context ▼ | | |
|---|---|---|
| Current context | | |
| Finding 1: Right breast mass, [obscured] o'clock | Finding 2: Right breast mass, 8 o'clock | Finding 3: Right breast mass, 9 o'clock |
| Modality ▾ ☑ MG<br>Body part ▾ ☑ MRI | Malignant mass, extensive segmental non-mass like enhancement medially | Benign intramammary lymph node |
| Heterogeneous, biopsy proven, malignant mass with irregular margins | | |
| Same obervations noted as without contrast | | |
| Palpable 1.5-cm spiculated mass, grade 3, biopsy recommended | | |
| MRI<br>5/10/2010 | | |
| MG<br>10/16/2009 | | |

CONTEXT DRIVEN SUMMARY VIEW OF RADIOLOGY FINDINGS

CROSS-REFERENCE TO PRIOR APPLICATIONS

This application is the U.S. National Phase application under 35 U.S.C. § 371 of International Application No. PCT/IB2014/060096, tiled on Mar. 24, 2014, which claims the benefit of U.S. Provisional Application No.61/806,550, filed on Mar. 29, 2013, These applications are hereby incorporated by reference herein.

BACKGROUND

Radiologists are required to work with an increasing number of images to diagnose and treat patients in an optimal manner. Patients such as, for example, cancer patients, frequently undergo numerous imaging exams, accumulating many studies in their medical records pertaining to the same anatomical region. Each time a new study needs to be read, the radiologist opens the current order to understand why the study has been performed and what prior findings the patient has. The imaging order, however, contains limited information related to findings such that the radiologist would need to open the results of the most relevant prior study to better understand the status of the patient's findings. This prior report, however, may not contain sufficient information about all the relevant findings, providing an incomplete overview of the patient's finding history. Thus, the radiologist is often required to open multiple prior reports and/or images and build mental links between related findings to obtain a complete picture of the patient's history. This process is difficult and time consuming. In addition, there are currently no quality assurance tools to ensure consistency and longevity of findings such that some previously identified findings may be overlooked. If findings are not followed-up on, as required, there may be potentially adverse effects on the patient outcome.

SUMMARY

A method for generating a context driven summary view of medical findings by retrieving a current study including at least one image to be analyzed, extracting current context information from the current study and storing the current context information in a database and matching the current context information with prior context information from prior studies to return a set of relevant prior studies.

A system for generating a context driven summary view of medical findings having a processor retrieving a current study including at least one image to be analyzed, extracting current context information from the current study and matching the current context information with prior context information from prior studies to return a set of relevant prior studies; and a memory storing the current and prior context information in a database.

A non-transitory computer readable storage medium with an executable program stored thereon, wherein the program instructs a processor to perform steps to generate a context driven summary view of medical findings. The steps including retrieving a current study including at least one image to be analyzed, extracting current context information from the current study and store the current context information in a database and matching the current context information with prior context information from prior studies to return a set of relevant prior studies.

DETAILED DESCRIPTION

The exemplary embodiments may be further understood with reference to the following description and the appended drawings wherein like elements are referred to with the same reference numerals. The exemplary embodiments relate to a system and method for reviewing a medical image. In particular, the exemplary embodiments describe extracting the context of a current imaging study to aid in reporting the results of the current imaging study. The context of the current imaging study may be used to generate a context-driven summary of prior studies, suggest templates/macros related corresponding to the current study and/or identify all related findings which should be reported on in a final report. Although the exemplary embodiments are specifically described in regard to reading images of cancer patients within a radiology department, it will be understood by those of skill in the art that the system and method of the present disclosure may be used for patients having any of a variety of diseases or conditions within any of a variety of hospital departments.

Figure 1:
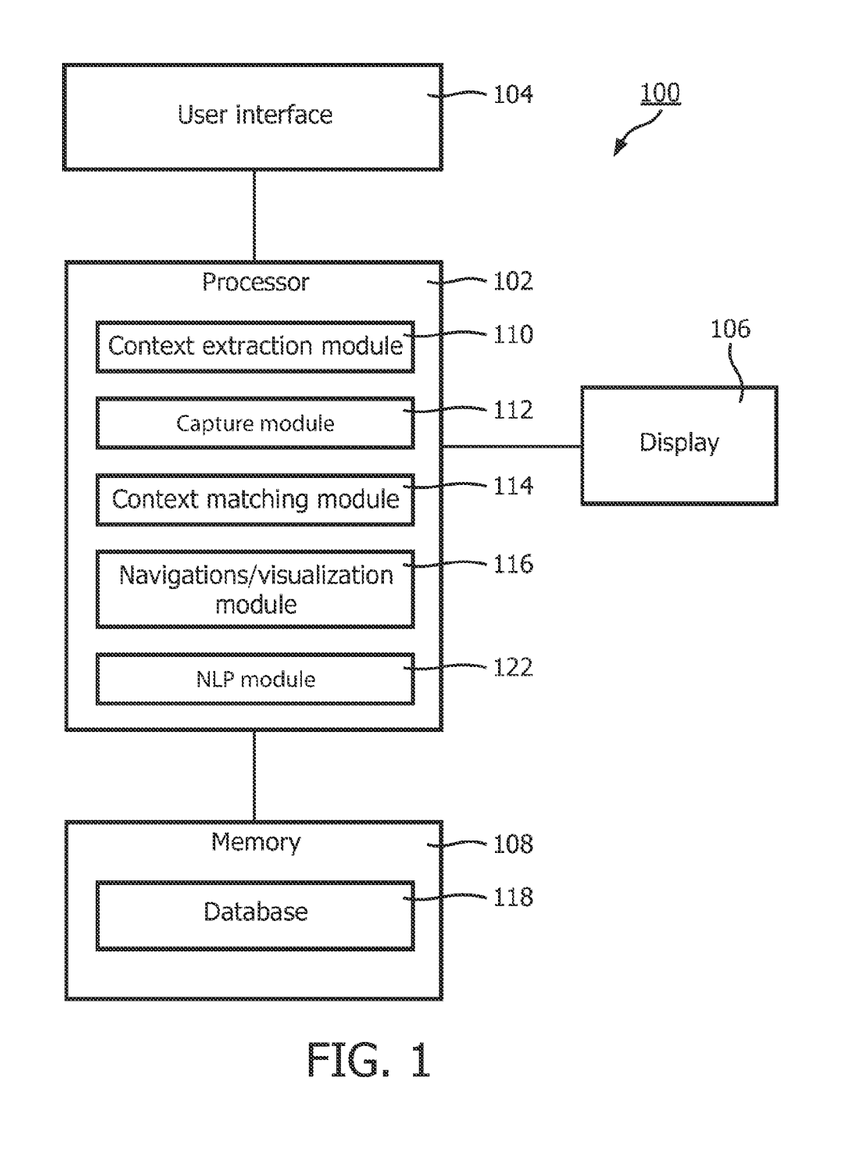
FIG. 1 shows a schematic drawing of a system according to a first exemplary embodiment.
Figure 2:
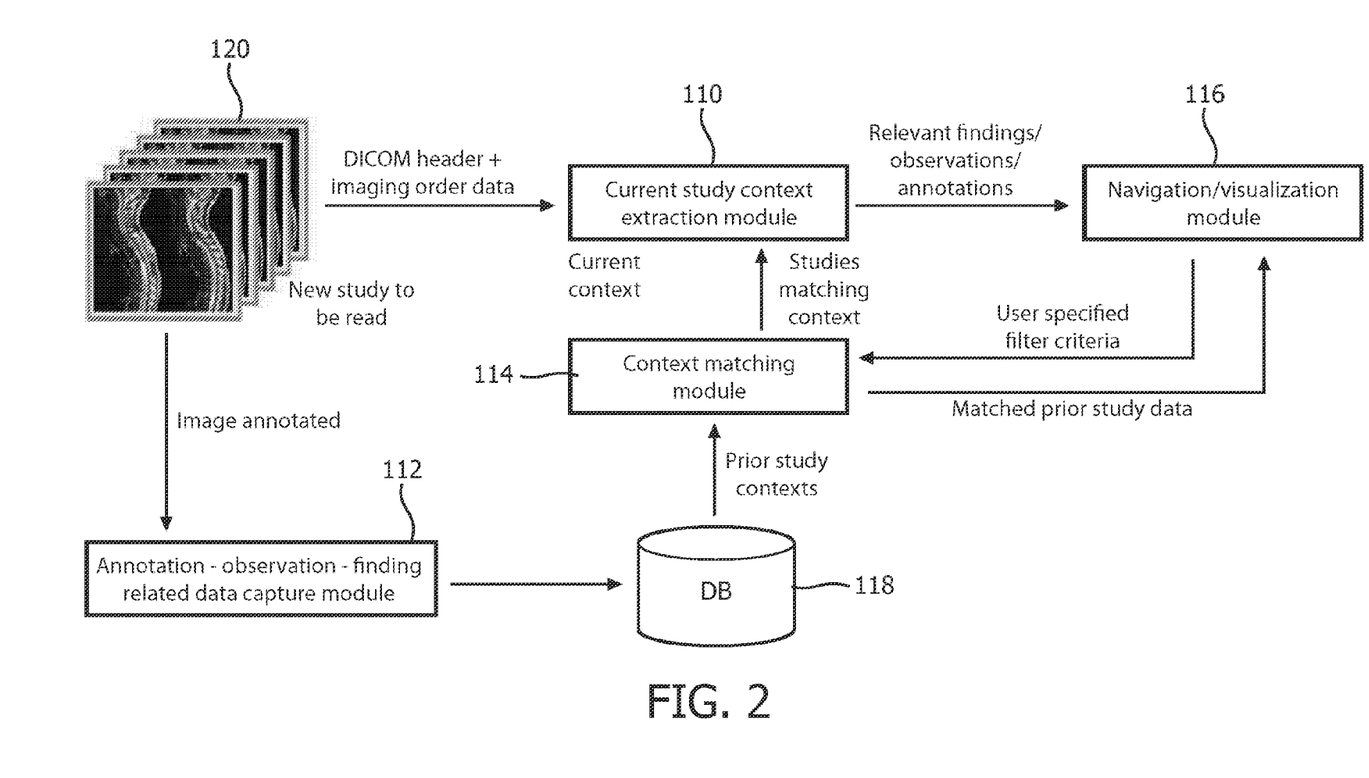
FIG. 2 shows another schematic drawing of the system of FIG. 1.

As shown in FIGS. 1 and 2, a system 100 according to an exemplary embodiment of the present disclosure generates a context driven summary view of prior related studies. The system 100 comprises a processor 102, a user interface 104, a display 106 and a memory 108. The processor 102 generates the summary view for a current study 120 including at least one image to be analyzed by extracting context information of the current study 120 using a context extraction module 110. The context extraction module 110 may also extract context information regarding the patient's clinical indications from an order of the current study 120. The context information may include data such as, for example, a modality (e.g., MRI, mammogram) and/or a body part (e.g., breast, head) imaged in the images of the current study 120. When the radiologist is rendering a diagnosis (i.e., the current study has not yet been reported), the context extraction module 110 may also extract context information including the patient's clinical indications from the image exam order of the current study. This context information is stored in a database 118 of the memory 108, which also stores finding (e.g., tumor) related information for current and/or prior studies of the patient. The database 118 may also store for example, annotations (i.e., mark-ups on an image) relating to the finding. The processor 102 further includes a capture module 112, which captures and stores information to the database 118 whenever a new annotation is created on the image by a user, and a Natural Language Processing (NLP) module 122 which extracts text data from the current study and/or prior reports.

The processor 102 also includes a context matching module 114 which matches the context extracted from the images of the current study 120 with all prior studies to determine which prior studies are related to the current study 120. In one example, current and/or prior study information may be displayed on the display 106 in a summary view. The summary view may, for example, show observations related to each of the findings and/or annotations on the images related to each of the findings. Once the summary view has been displayed, a navigation/visualization module 116 of the processor 102 permits a user to select a displayed observation and/or annotation to display further details of the selected finding. In another example, relevant prior studies may also be filtered to display a minimum set of findings that should be included in a report of the current study to maintain consistency and longevity of reports. In another exemplary embodiment, the context matching module 114 may also compare the context information of the current/prior studies with context information of templates and/or macros available for use by the user to return a set of relevant templates/macros. Thus, the user may easily select the templates/macros to cut down on reporting time. User selections may be made via the user interface 104, which may include input devices such as, for example, a keyboard, mouse, and/or touch display on the display 106.

Figure 3:
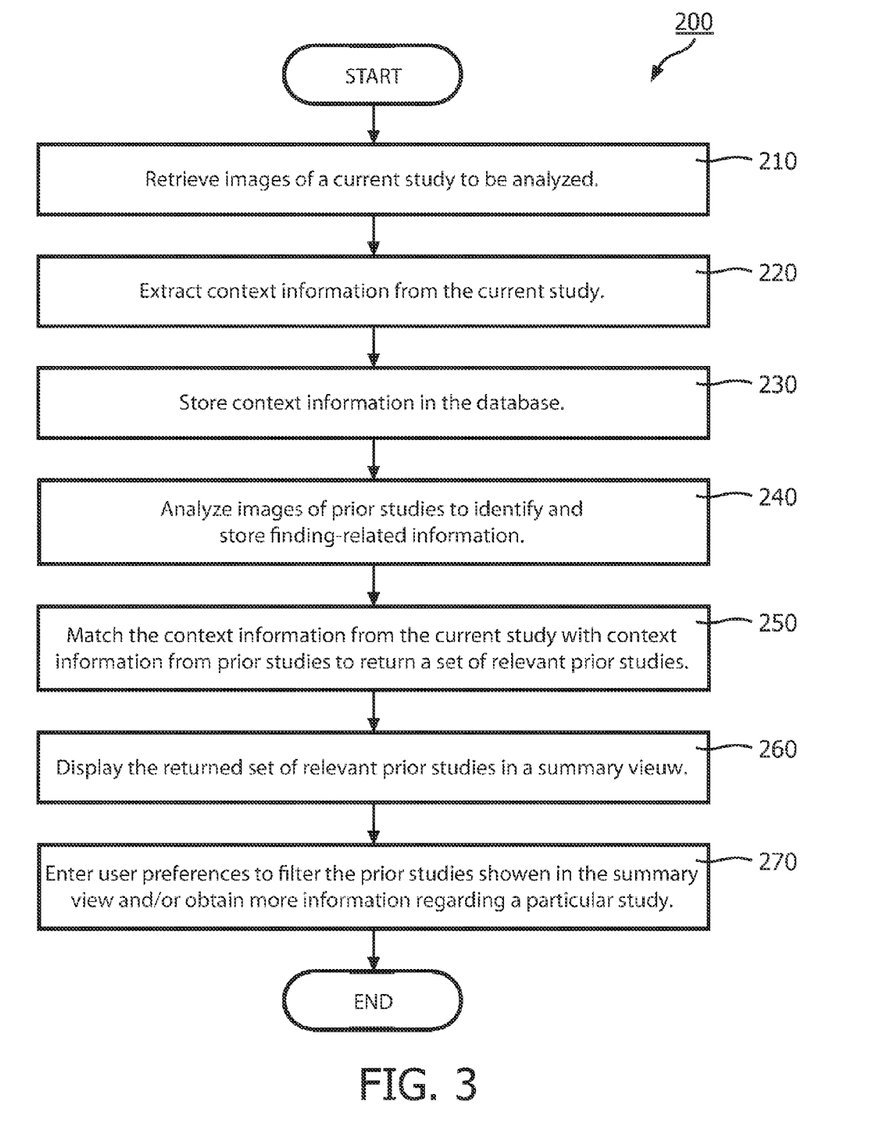
FIG. 3 shows a flow diagram of a method according to the first exemplary embodiment.

FIG. 3 shows a method 200 by which the summary view is generated. In a step 210, the system 100 retrieves the images to be analyzed in the current study 120. The images may be stored and viewed in, for example, a Picture Archiving and Communications System (PACS) within a Radiology Information System (RIS). In a step 220, the context extraction module 110 extracts content information from the images to be analyzed in the current study. As described above, the context information may include, for example, modality and/or body part. Images stored on the RIS/PACS system, for example, are stored and viewed in a DICOM (Digital Imaging and Communications in Medicine) file format, which includes a header containing information related to the modality and body part. When the radiologist or other user is rendering a diagnosis for the current study in which the image to be analyzed has not yet been reported, the context information may also include the patient's clinical indications from the imaging order of the current study. The extracted context information is then stored in the database 118, in a step 230. The database 118 also includes context information for images of prior studies, which may have been previously extracted and stored.

In a step 240, images of prior studies are analyzed by the capture module 114 to identify and store finding related information in the database 118. In the case of cancer patients, findings may include a tumor or mass identified in the images. Observations may include, for example, a description of the mass and/or a result of a biopsy of the tumor. Annotations for each of the observations and findings may be created on the image. Each time a new finding is created, the finding related information, including observations and annotations, are stored in the database 118. Each finding may have multiple observations associated with it. For example, the finding may be a first mass on a patient's left breast. The radiologist may input one or more observations regarding the first mass such as, for example, a designation of the mass as either malignant or benign and/or a description of the mass. Each observation may have one or more annotations on the image associated with it. The radiologist may also indicate that the annotations are for a new finding (e.g., a second mass) so that a new finding and observation are created. Alternatively, the radiologist may indicate that the annotation is associated with a new observation for an existing finding. Prior finding related information may also be stored by processing prior reports using a natural language processing (NLP) module 122 such as, for example, MEDLEE, so that findings from prior reports/studies may be quickly extracted. NLP modules alone provide only textual information of findings and will not show image annotations. The NLP module 122 may thus be combined with the above-described capture module 112 to extract both text and image data from prior studies. Finding related information of the current study is similarly generated and stored in the database 118. It will be understood by those of skill in the art that the finding related information of each study may be created and stored in the database 118 as each study is conducted and reviewed such that the finding related information may be stored in the database and later recalled when necessary.

In a step 250, the context matching module 114 compares the context information of the current study 120 with the context information of prior studies to return a set of matching prior studies. Context matching can be achieved using one of variety of matching techniques. In a first example, the context matching module 114 may utilize a rule-based approach in which the context matching module 114 first matches the studies to determine whether the modalities and body parts correspond. Second, the context matching module 114 extracts and compares protocol information of the current study and prior studies. Protocol information may include information such as, for example, whether contrast was applied, whether the study was lateral bilateral, left or right and, for cases in which the studies include MR images, the acquisition type (i.e., 2D/3D) and/or T1/T2. Third, the system 100 may extract information such as patient position and orientation from DICOM to determine whether it matches the position/orientation of the patient in prior studies.

In a second example, the context matching module 114 may utilize an ontology based approach in which a comprehensive ontology is used to determine whether context information of the current study matches context information of prior studies. The ontology may include anatomy and modality related information. For example, the anatomy may include body regions such as "Head and Neck" or "Abdomen and Pelvis" under which specific organs belonging to each region may be listed. For example, kidney and liver would be included under the "Abdomen and Pelvis" region. Using the ontology approach, the context matching module 114 may determine that a prior study matches the current study if the organs match one another. For example, if the context of the current study is the kidney, any prior studies having context information including the kidney, left kidney and/or right kidney would be returned as relevant.

In a third example, the context matching module 114 may utilize a data driven approach in which suitable contexts are determined by prior data. As described above in regard to the context extraction module 110 and the database 118, whenever a user selects or changes a context in the navigation/visualization module 116, these changes are stored and recorded in the database 118. For example, for a patient having lung cancer with brain metastasis, the current context may be the brain. However, prior lung related studies would also be relevant. Thus, a radiologist may select these other related studies when analyzing an image. The system 100 stores these selections in the database 118 such that once the system 100 has accumulated sufficient data, the context matching module 114 may automatically run data mining algorithms such as, for example, k-Nearest Neighbor and Mutual Information, to determine relevant studies. These algorithms may determine which contexts are most relevant given the current context.

In a fourth example, the context matching module 114 may utilize a hybrid approach in which any of the approaches described above may be combined. For example, the context matching module 114 may combine the rule based approach with the ontology based approach such that a semantic relationship between concepts is considered in addition to the matching of context such as modality and body part. Although four specific approaches are described above, it will be understood by those of skill in the art that the context matching module 114 may utilize any of a variety of matching techniques so long as the context matching module 114 is able to match the context information of the current study 120 with the context information of prior studies.

Figure 4:
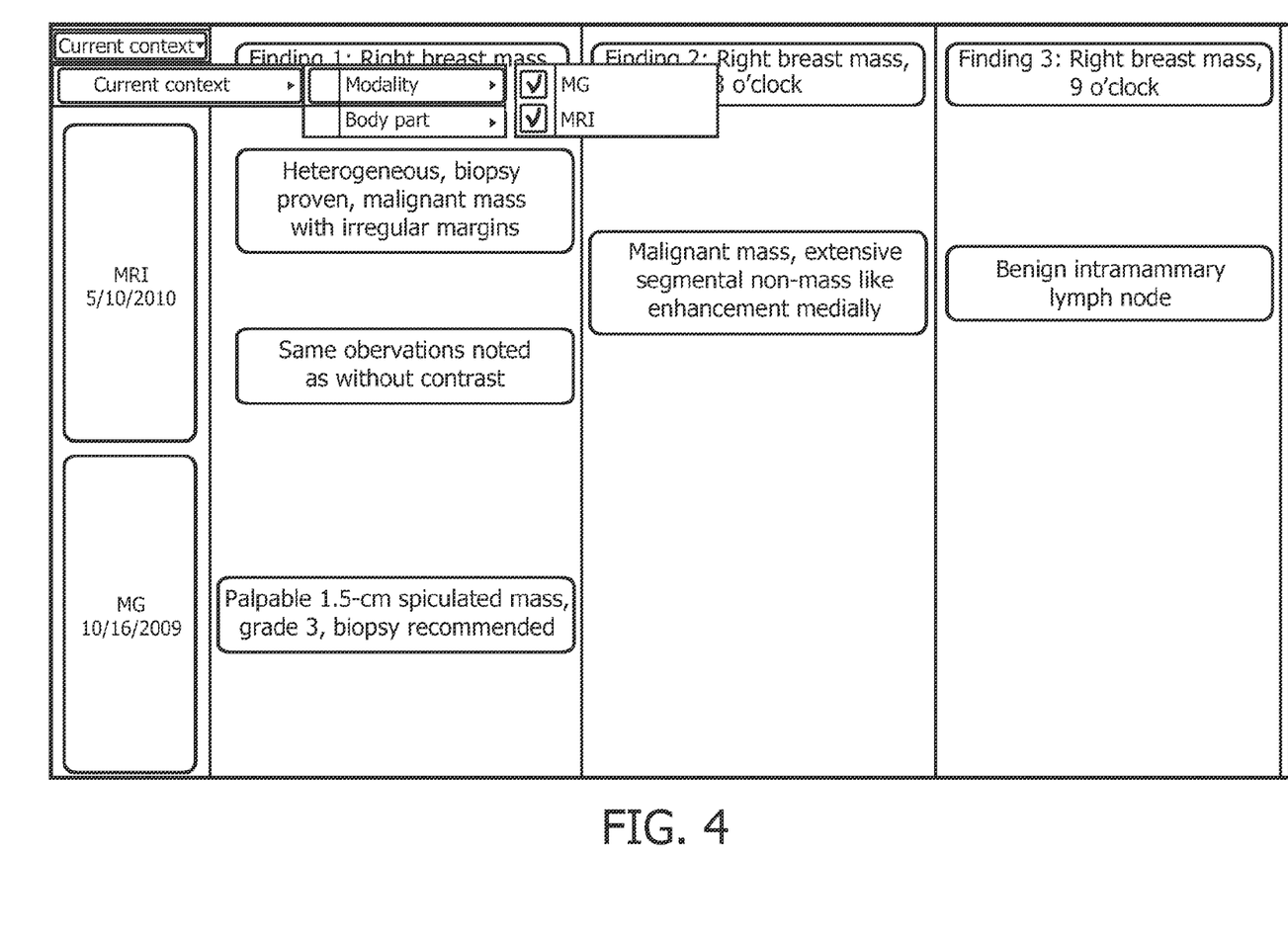
FIG. 4 shows an exemplary screenshot of a summary view displayed according to the method of FIG. 3.
Figure 5:
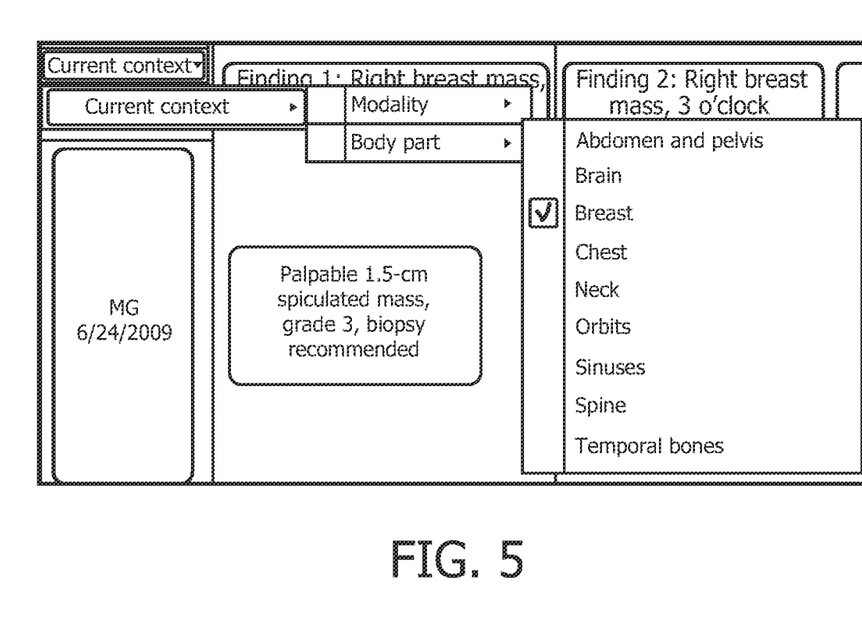
FIG. 5 shows another exemplary screenshot of the summary view of FIG. 4.

Once the context matching module 114 returns a set of matching prior studies, the navigation/visualization module 116 generates a summary view of the returned set of matching prior studies and displays the summary view on the display 106, in a step 260. As shown in FIG. 4, the summary view may, for example, show findings and the correlating observations for each of the related prior studies. In the exemplary case shown in FIG. 4, the patient had a mammogram in 2009, which resulted in a finding in the left breast. In 2010, an MRI was performed with and without contrast, resulting in two observations for this particular finding. Two additional findings, as shown in the second and third columns, were also discovered at this time. The current context is set to show modalities including mammograms and MRIs, as shown in FIG. 4, and the body part set to "breast," as shown in FIG. 5. The summary view provides a quick overview of the context-sensitive patient's findings, allowing the user to view the most recent and/or important related prior studies without having to read through multiple prior reports. The summary view also allows the user to visualize a progression of findings. For example, the user may easily determine how many new findings have been identified in the past two years, which would provide an indication of how rapidly a particular cancer is spreading.

Figure 6:
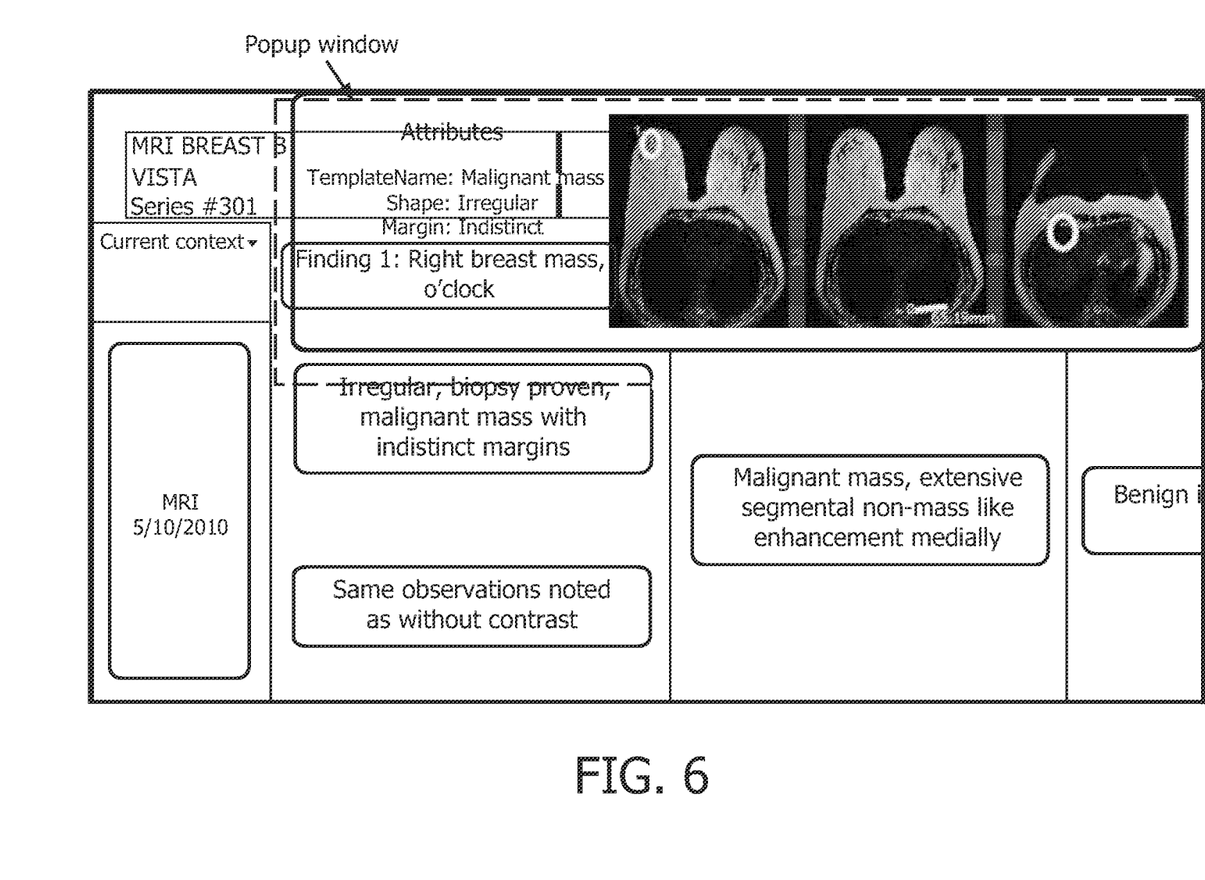
FIG. 6 shows an exemplary screenshot of key images displayed according to the method of FIG. 3.

In a step 270, the user may input user preferences via the user interface 104. The user may, for example, filter the prior studies shown in the summary view or indicate any desired changes to the current context via the user interface 104. For example, the user may expand or narrow the current context (e.g., narrow the current context to include only MRIs), indicate a number of prior studies to display in the summary view or indicate a desired period during which all displayed prior studies should fall. Other filters may include, for example, a type of lesion, which may include mass, symmetry and enhancement. The user may also navigate the prior studies to obtain more detailed information regarding that study. For example, the user may select an observation via a single mouse click to open the report corresponding to that particular study. Hovering the mouse over an observation may automatically show the corresponding key images for that study, as shown in FIG. 6. Double clicking one of these key images may automatically open a key images window such that the user may view these key images in their original size and/or resolution.

Figure 7:
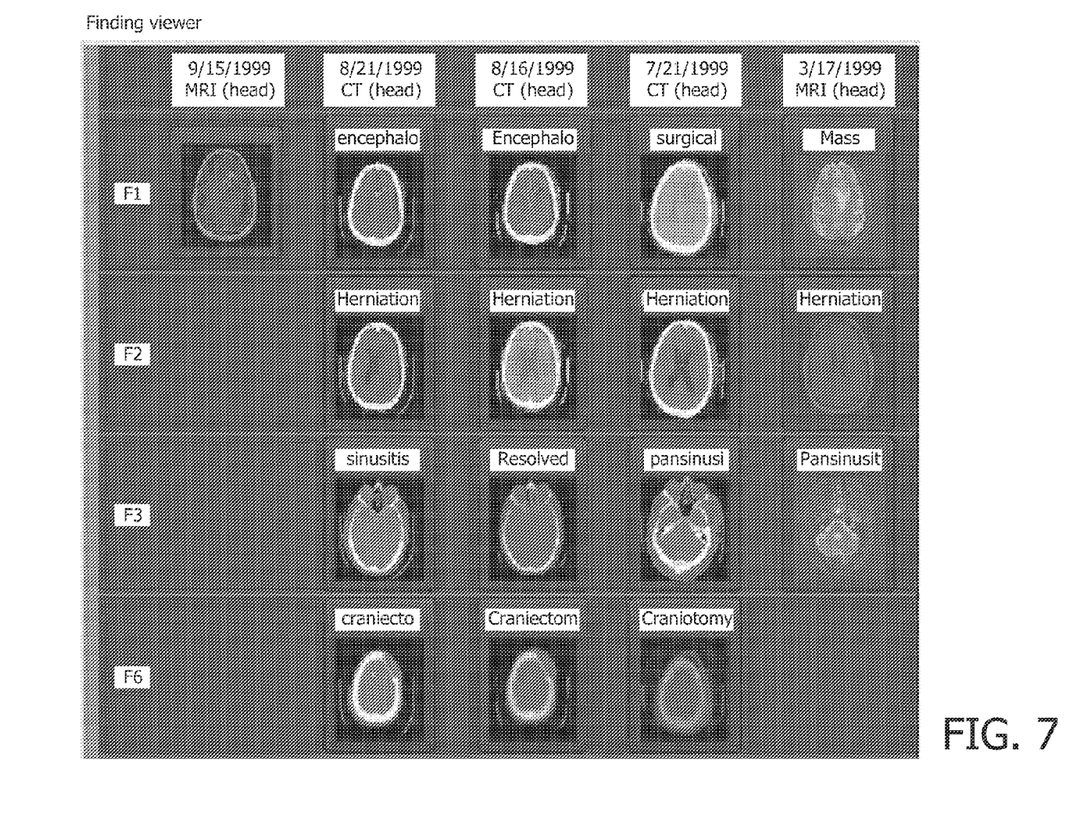
FIG. 7 shows an alternate exemplary screenshot of a summary view displayed according to the method of FIG. 3.

In an alternate embodiment, as shown in FIG. 7, rather than displaying the observations of relevant prior studies, the summary view may show images associated with each of the relevant prior studies. The images may also be shown with the annotations thereof such that selecting an image or annotation would open report and/or observation correlating to the selected image. It will be understood by those of skill in the art that the desired display (e.g., observations or images) may be indicated by the user as a user preference. The user may also indicate other preferences such as, for example, whether observations related to each of the findings should be displayed longitudinally, as shown in FIG. 4, or horizontally, as shown in FIG. 7. It will be understood by those of skill in the art that a variety of other user preferences for displaying the summary view, although not specifically described, are also possible.

Figure 8:
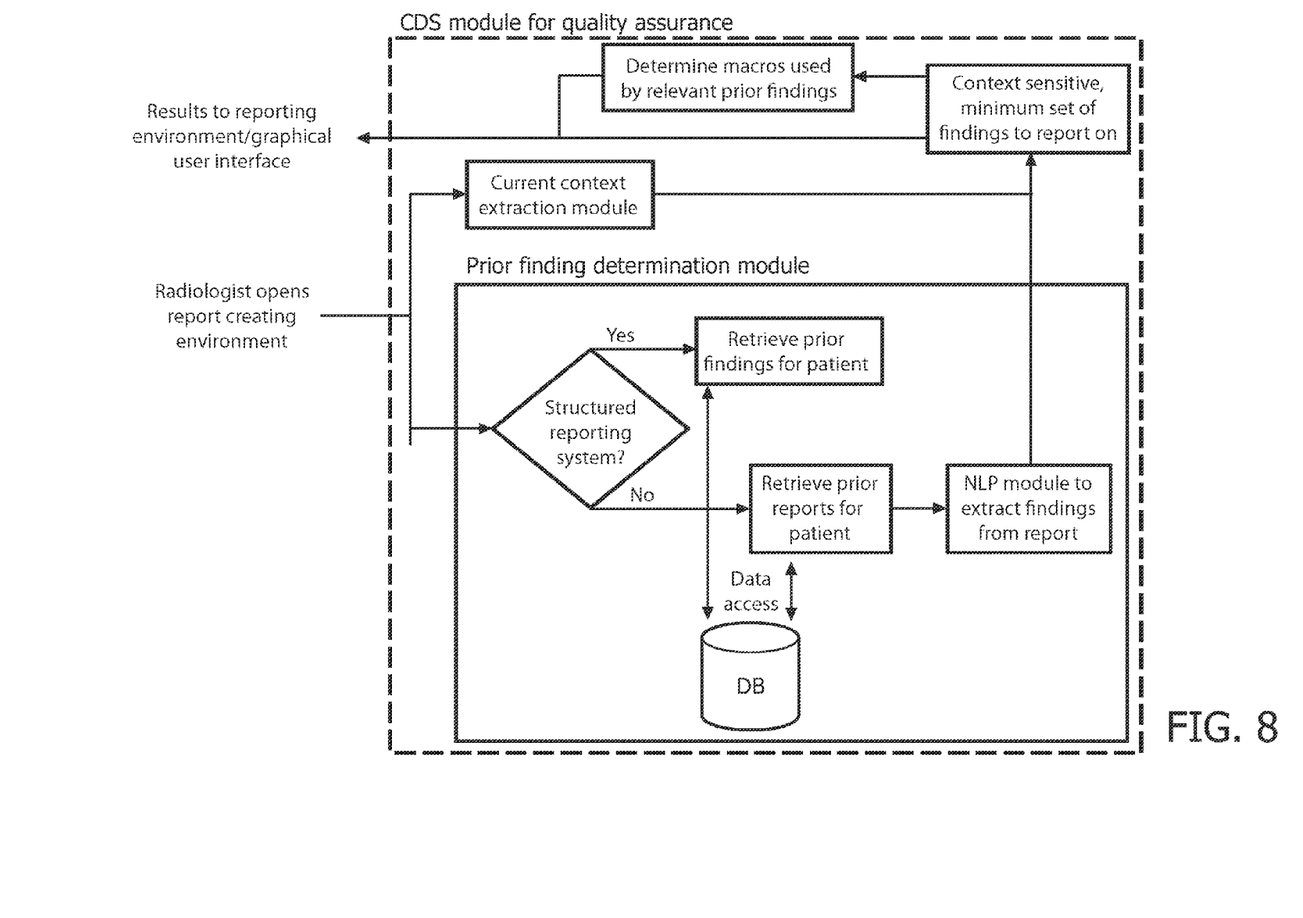
FIG. 8 shows a schematic drawing of a system and method according to a second exemplary embodiment.

According to another exemplary embodiment shown in FIG. 8, the system 100 may be utilized for quality assurance purposes by determining a minimum set of prior related findings which are required to be included in a report of the current study, as will be described in further detail below in regard to the method 300. Upon opening a report creating environment for the current study, the context extraction module 110 extracts context information from the current study to determine relevant prior findings via, for example, a prior finding determination module, which may include the capture module 112 for identifying and storing prior finding information to the database 118 where a structured reporting system has been utilized, the NLP module 122 for extracting finding information from text reports (e.g., from a non-structured reporting system) of prior studies and the context matching module 114 for comparing current context information to prior context information to identify the minimum set of findings required to be reported in the current study. Once the minimum set of findings has been identified, the processor 102 may also determine macros used by the relevant prior findings so that macros may be reused in the report for the current study.

Figure 9:
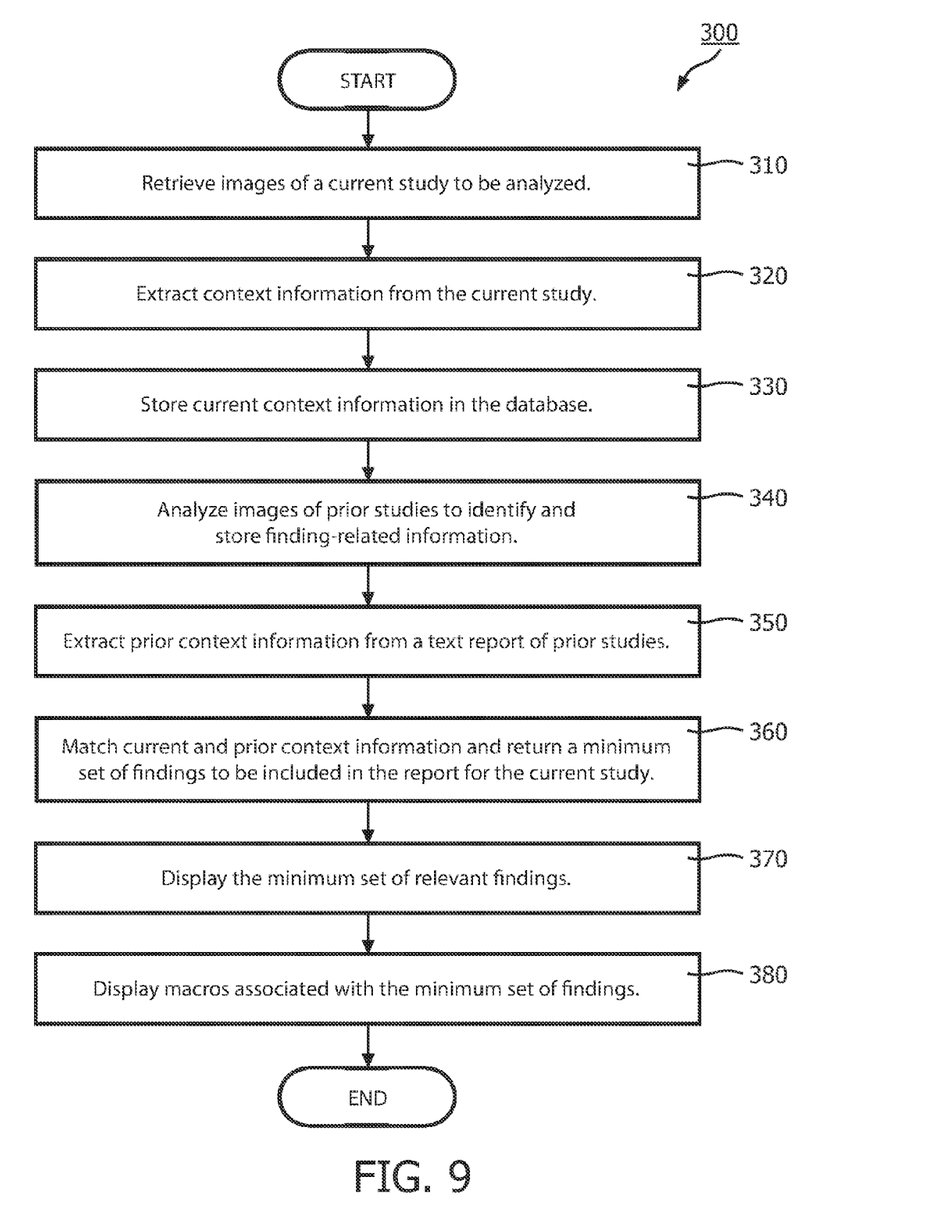
FIG. 9 shows a flow diagram according to the method of FIG. 8.

As shown in FIG. 9, a method 300 for identifying the minimum set of findings from the most recent, relevant prior study may be substantially similar to the method 200, described above. In particular, steps 310-340 are substantially similar to the steps 210-240 of the method 200. In step 310, the system 100 retrieves images of a current study to be analyzed and extracts context information from the current study using the context extraction module 110 in step 320. The context of the current study may be extracted in a manner substantially similar to the context extraction described in regard to the method 200. This context information is stored in the database 118, in step 330. In a step 340, finding related information of prior studies is identified and stored in the database 118, as described above in regard to the step 240. In the absence of a structured reporting environment, a full report of the prior study may be stored in the database 118. Alternatively, this information may be stored in a standard PACS format.

In a step 350, the NLP module 122 may extract a set of findings from an impressions section of a free-text radiology report of the prior studies. For example, if the prior report states, "There is a 16×11 mm diameter mass in the left cerebellopontine angle cisterns bulging into the ostium of the left internal auditory canal which is slightly hyperintense to brain on T2-weighted images and bright on the T1-weighted postcontrast images presumably due to homogeneous contrast enhancement," the NLP module 122 will determine that there is a finding of a 'mass in the left cerebellopontine' with an attribute diameter set to 16×11 mm. The NLP module 122 may be used in conjunction with the prior reports retrieved in the step 340.

In a step 360, the matching module 114 compares the current study context with contexts of the prior study, substantially as described above in regard to the step 250 of the method 200, to return a minimum set of findings required to be included in the report of the current study. Context matching may be performed using any of the approaches described above. For example, the matching module 114 may utilize any of a rule based approach, an ontology based approach, a data driven approach or a hybrid approach utilizing any combination of different matching processes. In a step 370, the processor 102 returns the minimum set of findings that should be included in the report of the current study. The navigation/visualization module 116 may display the minimum set of findings on the display via, for example, a graphical user interface, which also permits the user to filter and/or specify the findings to be returned in the minimum set. The default may be set to include findings of the most recent, relevant prior study. For example, if the current study is a liver study, the minimum set of findings will be based on the most recent liver study. This default setting may be easily changed by the user using the displayed graphical user interface. For example, where findings have been assigned a clinical significance score, the user may desire to report only the prior findings that have a minimum clinical significance score of 3. In another embodiment, in addition to or instead of displaying the returned relevant prior findings, an alert may be displayed to warn the user that the current report has been saved without including all prior findings that were deemed relevant in the step 370.

Once prior relevant studies have been identified, macros (e.g., predefined text which may be inserted into the report via a predefined name of the macro) or text fragments from the prior study may be utilized for the current study. In a step 380, macros/sentences that are associated with the minimum set of findings are listed on the display 106 for the user to review and use, as desired. Reusing macros/text provides consistency between reports and preserves the longevity of the findings. When a prior macro is reused, the processor 102 may automatically populate relevant fields (e.g., shape of the finding) of the finding in the current study based on the prior finding. The macros used in the relevant prior studies are stored in the database 118. Within a free text reporting environment, the text that contains the finding is used as the macro.

Macros may be particularly useful when using dictation systems in radiology reports. Radiologists use macros and templates (predefined document structures) to report observations quickly and efficiently. During dictation, the user speaks voice commands, which are matched to definitions of templates and macros so that the processor 102 may insert the predefined documents structure or text into the report. For example, when the user writes a report, the user may include five sections: procedure, clinical information, comparison, findings and impression. The Radiological Society of North America (RSNA) recommends information to be reported in each section according to modality, anatomy and clinical problems under investigation. For example, a template for a chest x-ray study may be as follows:

Procedure
Clinical Information
Cough
Fever
Shortness of Breath
Pre-operative Exam
Comparison
Findings
Heart
Lungs
Bones
Impression
Normal
No acute disease When using macros, the user defines the content and name of the macro. The content is a piece of text and the name is the voice command to insert the content to the report. For example, a macro describing gall bladder wall calcification could be: "Gall bladder wall calcification is present and consistent with a porcelain gall bladder, which is associated with an increased risk for development of gall bladder carcinoma." The name associated with this macro may be "porcelain gall bladder," such that when the user speaks "porcelain gall bladder," the processor 102 automatically inserts the above-defined text into the report.

Figure 10:
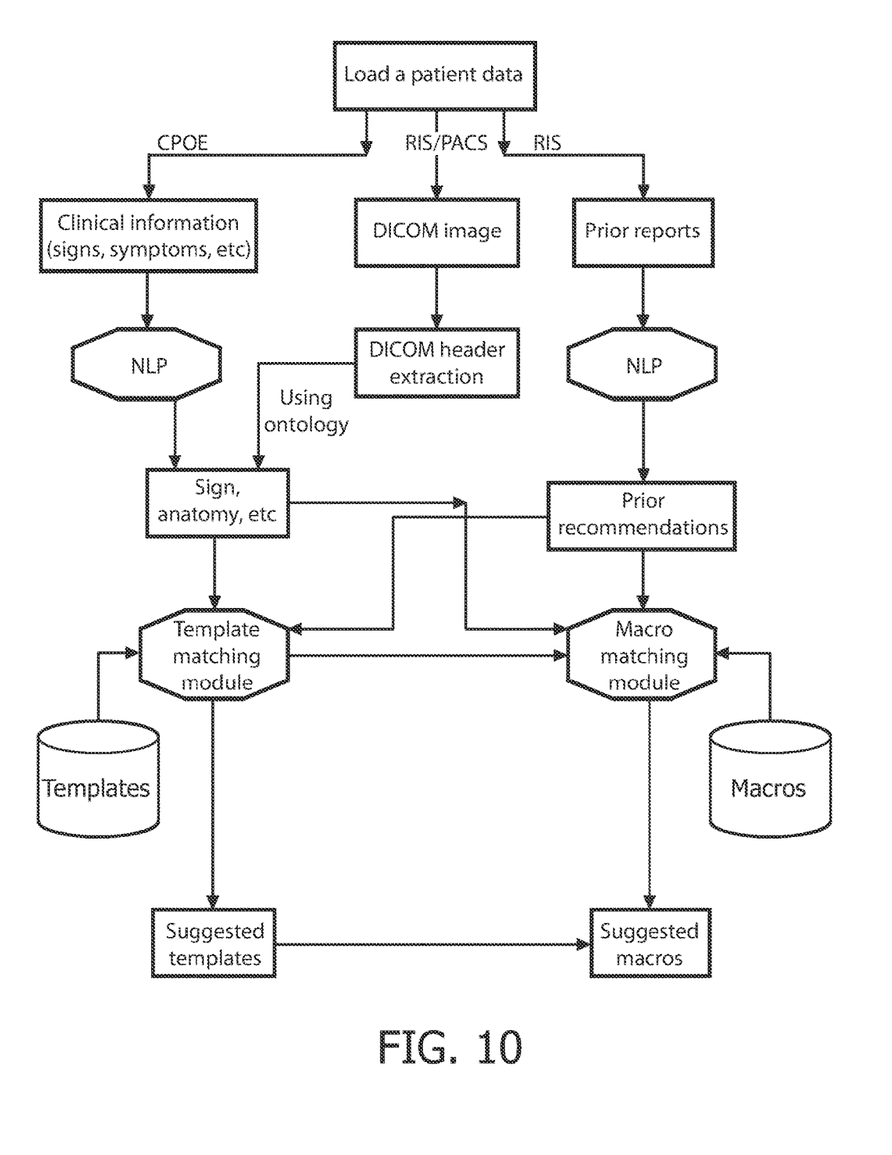
FIG. 10 shows a schematic diagram of a system according to a third exemplary embodiment.
Figure 11:
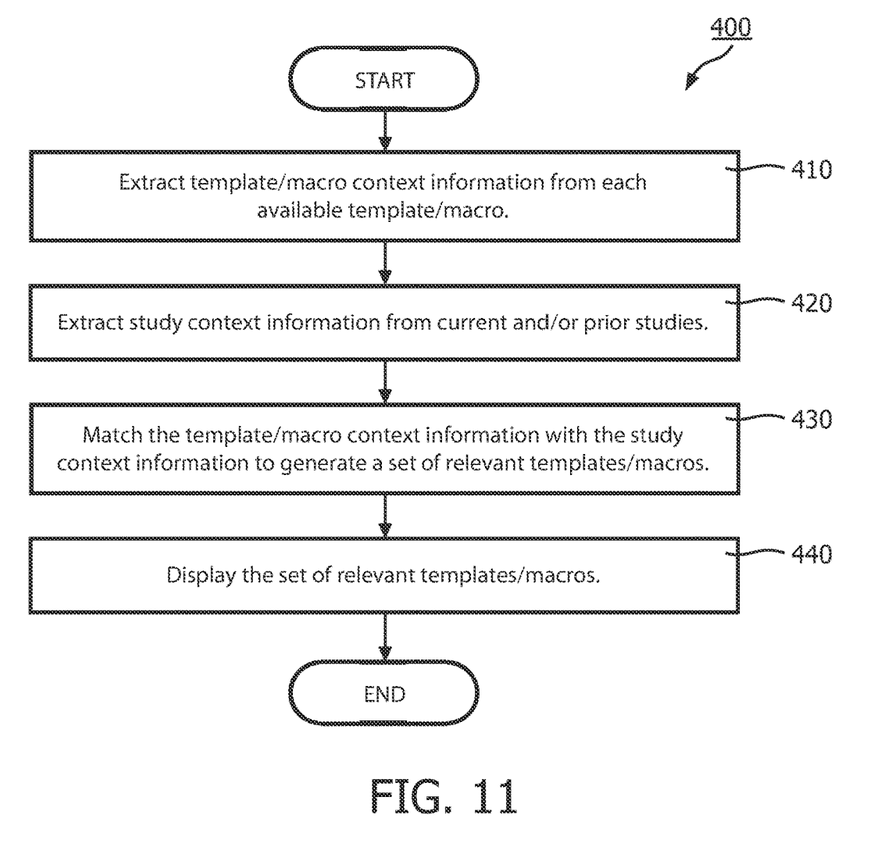
FIG. 11 shows a flow diagram of a method according to the third exemplary embodiment.

According to another exemplary embodiment, as shown in FIGS. 10 and 11, a method 400 generates a list of relevant templates/macros that the user may utilize for a current study using the system 100. As shown in FIG. 10, the context extraction module 110 and the NLP module 122 are used to extract context information from a current study (e.g., to extract information such as modality and body part), an image order for the current study (e.g., to extract clinical information such as signs and symptoms) and prior reports (e.g., to extract patient's recommendations). The extracted information may then be matched by the context matching module 114 to suggest relevant templates and/or macros. The memory 108 may further include available templates and macros in the database 118. Each template has a name and defines a set of sections in which findings will be inserted. Each macro has a name and defines a piece of text for insertion into the report.

In a step 410, as shown in FIG. 11, the NLP module 122 extracts context information from the narrative content of each reporting template/macro. For example, anatomy and diagnosis terms may be extracted from the templates/macros so that the system 100 associates a list of attributes to each template/macro. These attributes are stored in the memory 108 so that the templates/macros may be later recalled. In a step 420, the context information is extracted from a current study and/or relevant prior studies. The context information may be extracted substantially as described above in the step 220 of the method 200 and the step 320 of the method 300. For example, the context extraction module 110 may extract DICOM attributes if the study including body parts and modality. The NLP module 122 may further extract patient signs and symptoms from the reasons of exam section of the image order and/or patient's recommendation from relevant prior reports including: the date reported at each report, protocol/modality used in each report (e.g., MRI, Ultrasound), protocol/modality and date of the follow up exams (e.g., MRI 6 months) and findings of the image in each report (e.g., liver mass). The relevant prior reports may be identified, for example, by context matching between the current study and prior studies, as described above in regard to the methods 200 and 300.

In a step 430, the context matching module 114 compares the context information of the templates/macros obtained in step 410 with the context information of the current and/or prior relevant studies obtained in step 420 to generate a set of relevant templates/macros. The processor 102 may use any combination of rule-based, ontology and data driven (e.g., statistical) approaches, as described above in regard to the method 200. For example, the processor 102 may match context information from the current/prior studies (e.g., words related to clinical signs, anatomy and protocol) with the context information from the template/macro definitions. The system 100 may also use synonyms and acronyms or words in matching. For example, "MRI" is equivalent to both "MR" and "Magnetic Resonance Imaging." Using ontology based reasoning, the processor 102 matches, for example, an abdomen CT study with templates/macros related to the stomach, colon, liver, spleen, pancreas, kidney, bladder, etc. In another example, if the exam order includes a "follow-up," the processor 102 may match the follow-up with templates/macros related to follow-up using, for example, the NLP module 122. The processor 102 may also compare the date and/or protocol of the current study with the patient's recommendation information from prior reports. If there is a match, related templates/macros with the same findings may be ranked higher than others.

In a step 440, the navigation/display module 116 displays the relevant templates/macros to the user on the display 106. In one exemplary embodiment, only the relevant templates/macros are displayed. In another exemplary embodiment, templates/macros are listed in order of relevance with the most relevant templates/macros, for example, on the top of the list. In yet another exemplary embodiment, the list of available templates/macros may be displayed in, for example, alphabetical order, with the most relevant ones highlighted. It will be understood by those of skill in the art that the user may indicate his/her preferences for displaying the templates/macros via the user interface 104.

It is noted that the claims may include reference signs/numerals in accordance with PCT Rule 6.2(b). However, the present claims should not be considered to be limited to the exemplary embodiments corresponding to the reference signs/numerals.

Those skilled in the art will understand that the above-described exemplary embodiments may be implemented in any number of manners, including, as a separate software module, as a combination of hardware and software, etc. For example, the context extraction module 110, the capture module 112, the context matching module 114, the NLP module 122 and the navigation/visualization module 116 may be programs containing lines of code that, when compiled, may be executed on a processor.

It will be apparent to those skilled in the art that various modifications may be made to the disclosed exemplary embodiments and methods and alternatives without departing from the spirit or scope of the disclosure. Thus, it is intended that the present disclosure cover the modifications and variations provided that they come within the scope of the appended claims and their equivalents.

What is claimed is:

1. A method for using macros related to a current medical study of a patient with steps executable by a processor, the steps comprising:
    retrieving the current medical study of the patient including at least one image to be analyzed;
    extracting current context information from the current medical study and storing the current context information in a database;
    comparing the stored current context information to prior context information from prior studies and matching the current context information with prior context information from prior studies to identify a minimum set of findings required to be reported in the current study, the minimum set of findings including the most recent prior studies of the patient;
    extracting macro context information from available macros, wherein each macro comprises predefined text which may be inserted into the current medical study;
    matching the macro context information with the context information of the prior relevant studies to generate a list of relevant macros associated with the minimum set of findings required to be reported in the current study, wherein the matching the macro context information with the context information includes an ontological approach;
    displaying the generated list of relevant macros in order of relevance wherein the most relevant macro is highlighted; and
    inserting the predefined text of the highlighted macro into the current medical study of the patient in response to a user selection; wherein the user selection is made via a user interface and comprises one or more of the relevant macros.

2. The method of claim 1, further comprising:
    displaying a summary view of the set of relevant prior studies including finding related information for each of the relevant prior studies.

3. The method of claim 1, further comprising:
    filtering the summary view based on a user preference.

4. The method of claim 3, wherein filtering the summary view includes one of modifying a current context, identifying a type of lesion, identifying a time period within which displayed prior studies should fall and indicating a number of prior studies to be shown.

5. The method of claim 1, further comprising:
    analyzing images of prior studies to identify and store the finding related information.

6. The method of claim 5, wherein the finding related information includes one of an observation describing the finding and an annotation on an image associated with the observation.

7. The method of claim 6, wherein the displayed summary view shows one of observations and key images related to a finding of each prior relevant study.

8. The method of claim 1, wherein matching the current context information with the prior context information includes at least one of a rule based approach, an ontology approach and a data driven approach.

9. The method of claim 1, further comprising:
    selecting finding related information of one of the relevant prior studies to display further information corresponding to the selected prior relevant study.

10. A non-transitory computer readable storage medium with an executable program stored thereon, wherein the program instructs a processor to perform a method as defined in claim 1.

11. A system for suggesting macros related to a current medical study of a patient, comprising:
    a processor configured for
    retrieving the current medical study of the patient including at least one image to be analyzed, extracting current context information from the current medical study and matching the current context information with prior context information from prior studies to identify a minimum set of findings required to be reported in the current study, the minimum set of findings including the most recent prior studies of the patient;
    extracting macro context information from available macros;

comparing the stored current context information to prior context information from prior studies and matching the macro context information with the context information of the prior relevant studies to generate a list of relevant macros associated with the minimum set of findings required to be reported in the current study, wherein the matching the macro context information with the context information includes an ontological approach, a rule-based approach, a data driven approach which executes data mining algorithms for determining prior relevant studies, or a combination thereof, displaying, on a display, the generated list of relevant macros in order of relevance wherein the most relevant macro is highlighted; and using the highlighted macro in the current medical study of the patient in response to a user selection; wherein the user selection is made via a user interface and comprises one or more of the relevant macros; and a memory storing the current and prior context information in a database.

12. A method for suggesting macros or text fragments related to a current medical study of a patient, comprising:

retrieving the current medical study of the patient including at least one image to be analyzed;

extracting current context information from the current medical study and storing the current context information in a database;

comparing the stored current context information to prior context information from prior studies and matching the current context information with prior context information from prior studies to identify a minimum set of findings required to be reported in the current study, the minimum set of findings including the most recent prior studies of the patient;

identifying and listing macros or text fragments used in the relevant prior studies, wherein the identifying and listing macros or text fragments includes an ontological approach; and displaying, on a display, the list of macros or text fragments associated with the minimum set of findings required to be reported in the current study in order of relevance wherein the most relevant macro or text fragment is highlighted; and using the highlighted macro or text fragment for the current medical study of the patient in response to a user selection; wherein the user selection is made via a user interface and comprises one or more of the relevant macros, automatically populating relevant fields related to a medical finding in the current medical study based on a finding from a prior study.

13. A system for suggesting macros or text fragments related to a current medical study of a patient, comprising:

a processor configured for retrieving the current medical study of the patient including at least one image to be analyzed, extracting current context information from the current medical study with natural language processing;

comparing the stored current context information to prior context information from prior studies and matching the current context information with prior context information from prior studies to identify a minimum set of findings required to be reported in the current study, the minimum set of findings including the most recent prior studies of the patient, identifying and listing macros or text fragments used in the relevant prior studies, wherein the identifying and listing macros or text fragments includes an ontological approach; and displaying, on a display device, the list of macros or text fragments associated with the minimum set of findings required to be reported in the current study in order of relevance wherein the most relevant macro or text fragment is highlighted, wherein the displayed list of macros or text fragments are selectable by the user; and using the highlighted macro or text fragment for the current medical study of the patient in response to a user selection; wherein the user selection is made via a user interface and comprises one or more of the relevant macros; and a memory storing the current and prior context information in a database.

14. The system according to claim 13, wherein using the highlighted macro or text fragment includes automatically populating relevant fields related to a medical finding in the current medical study based on a finding from a prior study.

15. The system according to claim 14, wherein the medical finding is related to a shape of an anatomical structure.

16. The system according to claim 13, wherein the comparing step is performed to identify a minimum set of findings required to be reported in the current study and the displayed list of macros or text fragments is associated with the minimum set of findings required to be reported in the current study.

17. The system according to claim 13, wherein if a report is saved without the minimum set of findings required to be reported, an alert is sent to a user.

* * * * *